United States Patent [19]

Ansorge

[11] Patent Number: 4,460,525

[45] Date of Patent: Jul. 17, 1984

[54] METHOD FOR PREPARING THIN LAYERS

[75] Inventor: Wilhelm Ansorge, Gaiberg über Heidelberg, Fed. Rep. of Germany

[73] Assignee: Europaisches Laboratorium Fur Mokekularbiologie (EMBL), Heidelberg, Fed. Rep. of Germany

[21] Appl. No.: 275,894

[22] Filed: Jun. 22, 1981

[30] Foreign Application Priority Data

Jun. 27, 1980 [DE] Fed. Rep. of Germany ....... 3024288

[51] Int. Cl.³ .............................................. B29C 1/02
[52] U.S. Cl. ..................... 264/39; 264/259; 264/261; 264/299
[58] Field of Search ................. 264/39, 299, 259, 261

[56] References Cited

U.S. PATENT DOCUMENTS 4,246,222  1/1981  Monthony ........................... 264/299

*Primary Examiner*—James H. Derrington
*Attorney, Agent, or Firm*—Wood, Dalton, Phillips, Mason & Rowe

[57] ABSTRACT

A method and apparatus for preparing thin layers, such as thin gel layers useful in electrophoresis, wherein a liquid layer material is introduced to the space defined between two parallel mold surfaces on first and second mold elements. Initially, the mold surfaces overlap each other to a small extent, and liquid is introduced to the space between the surfaces adjacent the leading edge of the top mold element. The mold elements are then shifted with respect to each other while maintaining their parallel relationship, and additional liquid layer-forming material is introduced to the space during the shift. In a preferred embodiment, a third mold element is situated adjacent to and spaced a small distance from the bottom mold element, and liquid material is introduced to the space between the bottom mold elements during shifting of the top mold.

31 Claims, 6 Drawing Figures

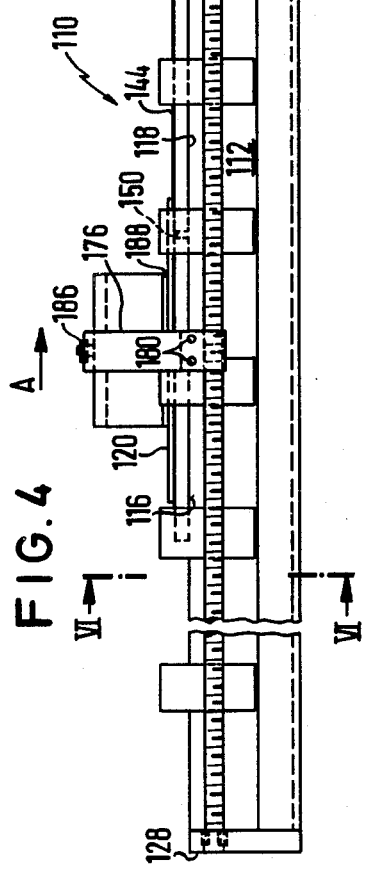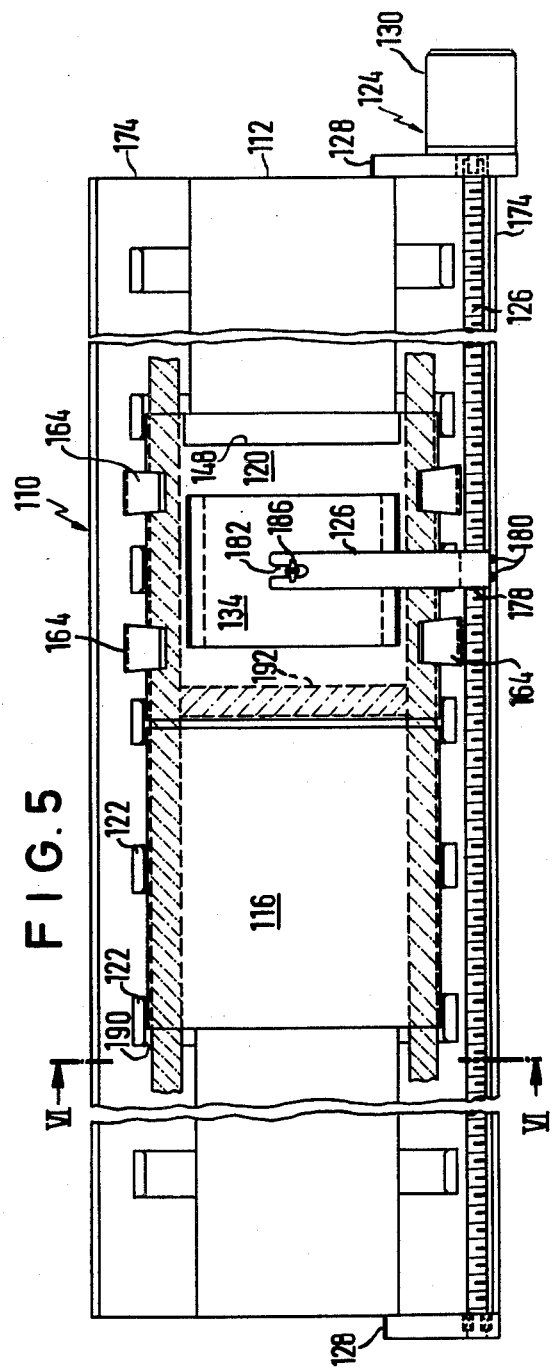

METHOD FOR PREPARING THIN LAYERS

BACKGROUND OF THE INVENTION

1. Field of the Invention

This invention relates generally to the formation of thin layers and, more specifically, this invention relates to a method and apparatus for preparing thin layers, such as gel layers useful in electrophoresis.

2. Description of the Prior Art

Among other purposes, thin gel layers are used in zone electrophoresis, especially for DNA sequencing, SDS gel electrophoresis (SDS PAGE) and isoelectric focusing. In these techniques small gel layer thicknesses are advantageous, since the temperature gradient over the layer thickness is small, and because the Joule heat per unit area and unit electric field are also small, therefore permitting high fluid strengths. Also, the time required for staining and destaining is relatively short when thin layers are used. Finally, because only small amounts of sample material are necessary with thin layers, sensitivity is enhanced.

In one known process of preparing gel layers, a liquid layer-forming material is poured from overhead into a perpendicularly arranged finished casting mold. However, this prior process has been found to be unsuitable for the preparation of bubble-free gel layers with a thickness of less than approximately 0.4 mm.

SUMMARY OF THE INVENTION

It is an object of the invention to provide a method and apparatus for preparing thin, bubble-free layers, such as thin gel layers useful in electrophoresis.

According to the present invention, a first mold element having a first mold surface and a second mold element having a second mold surface parallel to the first mold surface are shifted relative to each other in a longitudinal direction from an initial position, in which the parallel mold surfaces slightly overlap, and are spaced from each other by a small distance, to a final position, in which the mold surfaces are opposite each other. A liquid layer material is introduced to the space defined between the mold surfaces, near the leading edge of the first mold element, both in the initial position and during the parallel shift. The leading edge is perpendicular to the direction of shift and its opposite the second mold surface in the initial position of the mold elements.

The process of the invention is preferably carried out in a horizontal apparatus having the first mold element disposed above the second mold element, and by applying the liquid layer material to the second mold surface by dropwise addition.

The preferred apparatus comprises a horizontal support for the second mold element and, if desired, a third mold element, with guide means disposed at opposite sides of the support, with the first mold element mounted between the guide means for shifting therebetween.

By shifting the mold elements over each other with simultaneous introduction of the liquid layer-forming material into the space between the mold surfaces, very thin, bubble-free layers can readily be prepared with thicknesses as low as 0.02 mm. Thicker layers up to 1.5 mm can also be produced. The proposed process is extremely simple and can be readily performed even by unskilled persons. The required processing time is short.

For example, approximately one minute is required for the preparation of a 200 mm long gel layer.

In the case of the low layer thicknesses, the capillary effect between the mold surfaces is so strong that the liquid layer material remains between the horizontal mold surfaces without the aid of special seals. With the process of the invention, gel layers with specified properties can be prepared with good reproducibility. The process can be used without difficulty for gel layers having either high or low monomer concentrations. Gel layers with a large surface area, for example with a length of greater than 200 mm and a width greater than 20 mm, can be readily repaired.

Further objects and advantages will be apparent to those skilled in the art from the following detailed description, the drawings and the appended claims.

BRIEF DESCRIPTION OF THE DRAWINGS

FIG. 4 is a side view of a second embodiment of the apparatus of the invention;

FIG. 5 is a top plan view of the apparatus of FIG. 4; and

DETAILED DESCRIPTION OF THE INVENTION

Figure 1:
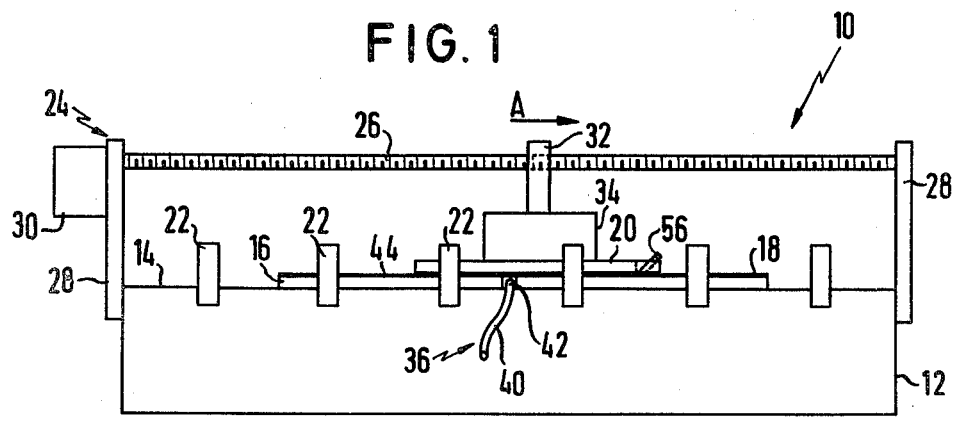
FIG. 1 is a schematic elevation of a preferred embodiment of the apparatus for preparing thin layers according to the invention.
Figure 2:
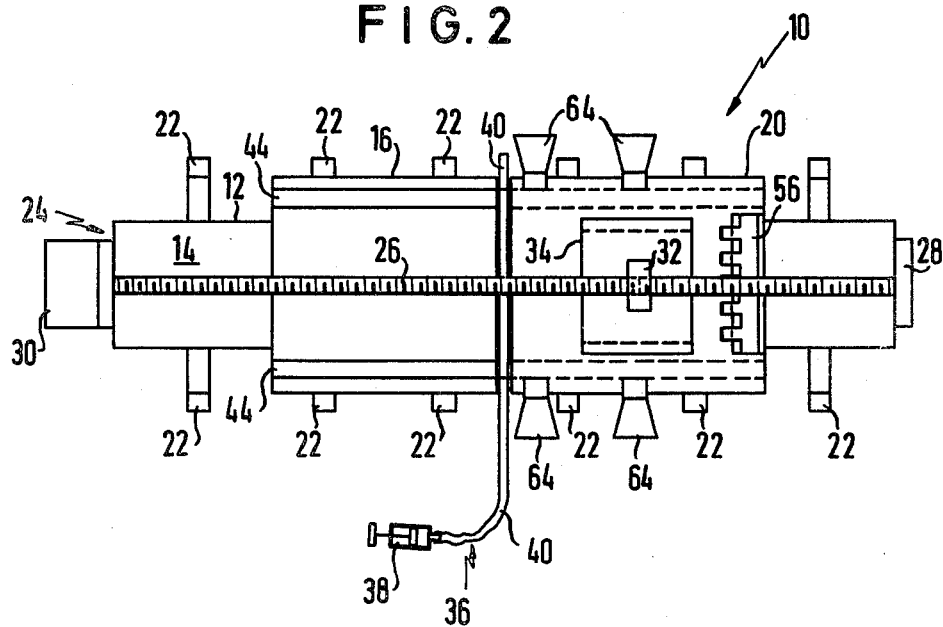
FIG. 2 is a top plan view of the apparatus of FIG. 1.
Figure 3:
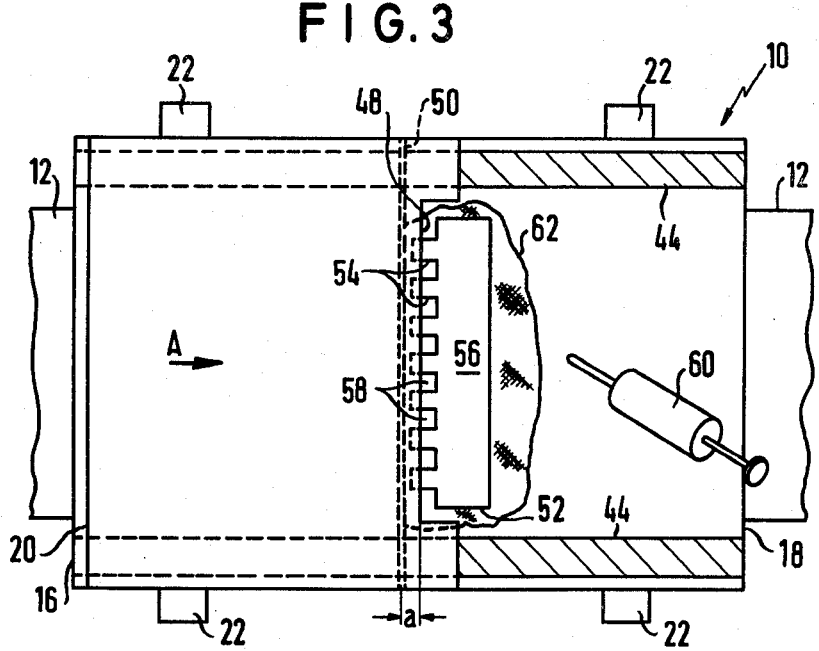
FIG. 3 is an enlarged top plan view of the apparatus of FIGS. 1 and 2 during the introduction of the layer-forming material, with parts broken away for clarity.

Referring first to FIGS. 1–3, a preferred embodiment of the apparatus for preparing thin layers according to the invention is generally designated 10. The apparatus 10 comprises an elongate support 12 having a horizontal upper side 14. Two rectangular glass plates 16 and 18 are disposed on the upper side 14 and are spaced a small distance from each other.

The plates 16 and 18 have identical dimensions. A third glass plate 20 is disposed over the plates 16 and 18, and is moved with the aid of a drive, to be described below, from the initial position shown in FIG. 3, through the intermediate position shown in FIG. 1 and the final position shown in FIG. 2. In the final position of FIG. 2, the plates 18 and 20 are spaced a small distance from each other and form a mold for a liquid layer material which is introduced to the space between the two plates 18 and 20 as described below. The gap between the plates 16 and 18 must not be so small as to result in aspiration of gel from between the mold surfaces by capillary action.

The layer material, preferably a gel, will ultimately be polymerized between the plates 18 and 20. Hereinafter, the upper plate 20 will be referred to as the first mold plate and the lower plate 18 will be referred to as the second mold plate. The plate 16 of FIGS. 1–3 will be referred to as the auxiliary plate.

The plates 16, 18 and 20 are each fitted between lateral guide means 22, which are disposed on the long sides of the support 12. Use of the guides 22 dispenses with the necessity of special holders. The auxiliary plate 16 and the second mold plate 18 are fixed to the upper side 14 of support 12. The first mold plate 20 can be moved between the lateral guides 22 in the direction of arrow A in FIG. 1, and in the opposite direction.

The first mold plate 20 is preferably moved from its initial position of FIG. 3 to its final position of FIG. 2 with the aid of a spindle drive, generally designated 24. The spindle drive 24 comprises a threaded spindle 26 which is disposed above the support 12 parallel to the longitudinal direction of the support 12 and is rotatably supported at both ends by sole plates 28 which are attached to the support 12. The threaded spindle 26 is driven by an electric motor 30 at the left end of the spindle 26 in FIGS. 1 and 2. A driver 32 runs without torsion on the threaded spindle 26, and is rigidly attached to the upper side of a bridge 34, which is attached to the first mold plate 20. Consequently, when the threaded spindle 26 is turned, the mold plate 20 is shifted in the direction of arrow A through the driver 32 and bridge 34.

An inlet for additional layer material, generally designated 36, is shown schematically in FIGS. 1 and 2. (For clarity, the inlet 36 is omitted in FIG. 3.) As shown schematically in FIG. 2, the inlet 36 comprises a pump 38 (omitted in FIG. 1) in the form of a syringe, which pumps the gel into a perforated thin tube 42 through flexible tubing 40. The inside diameter of the tube 42 can be, for example, 1.5 mm. The tube 42 fills the gap between the auxiliary plate 16 and the second mold plate 18.

A low friction sealing strip 44 is placed over each plate 16 and 18 near the side edges thereof which are parallel to the direction of movement A (see FIGS. 2 and 3). These sealing strips are preferably of polytetrafluoroethylene (Teflon) and the thickness of each sealing strip 44 corresponds to the desired thickness of the thin layer to be prepared.

As mentioned above, the mold plates 18 and 20 and auxiliary plate 16 are preferably of glass, which is an especially suitable carrier for gels, such as polyacrylamide gels. Further, glass plates permit ready observation of the gel, and are readily obtainable with the required surface quality. Foils of polyester and polystyrene, in addition to glass, are especially useful, since after the surface treatment the gels adhere onto them. The plates 18 and 20 can be subjected to a surface treatment, described in the Example, below, as a result of which the polymerized gel will adhere well to either one of the plates 18 or 20 through covalent adhesive forces. Additionally, cellophane and polyamide fiber fabric (nylon) materials are suitable as plate materials. Such materials are electrical insulators, have reasonably good thermal conductivity, are transparent, are inert toward staining dyes, are resistant to chemicals, exhibit good dimensional stability. Further, these materials are flexible, and permit parts of the gel to be cut and removed, if desired.

Bubble-free gel layers having a thickness between about 0.02 mm and 1.5 mm can be readily prepared with the apparatus of FIGS. 1-3. Such thin gel layers are especially useful in electrophoresis devices as, for example, in the separation of biological macromolecules.

After pretreatment of the mold surfaces of the first and second mold plates 18 and 20, as described below, the second mold plate 18 is placed on the support 12 adjacent the auxiliary plate 16. If desired, a thermostatically heatable plate can be used as the second mold plate 18, thus permitting the heating of the gel layer to a uniform temperature in the electrophoresis measuring device. A polyester film gel support can be provided between the heatable plate and the gel layer or between the gel layer and the first mold plate 20, if desired.

In the latter case, the polyester film does not prevent heat supply to the gel layer from the heatable plate. To attach the film to the plate, a few drops of a 5% glycerol solution are placed into the mold surface of the heatable plate or the mold surface of the first mold plate 20 and then the polyester film is rolled onto the plate with the aid of a rubber roller. The free surface of the polyester film is subjected to the surface treatment for improvement of gel adhesion referred to above and described below.

The thickness of the auxiliary plate 16 is identical to that of the second mold plate 18 so that the top surfaces thereof lie in the same plane. The two sealing strips 44 described above are placed on the side edges of each plate 16 and 18 parallel to the direction of movement A. The first mold plate 20 is then placed onto the sealing strips 44, with its pretreated surface (the first mold surface) facing downward, and fitted between lateral guides 22.

In its initial position (FIG. 3), the first mold plate 20 lies on sealing strips 44 and mostly over the auxiliary plate 16, but it extends slightly above the second mold plate 18, overlapping with it over a length a, which may be on the order of 5 mm (see FIG. 3). The overlapping length a is the distance between the closest edges of the plates which extend transversely to the direction of movement A, namely between leading edge 48 of the upper, first mold plate 20 and the trailing edge 50 of the lower, second mold plate 18.

If the overlap a is greater than about 15 mm, the capillary effect between the plates 18 and 20 will be insufficient to instantaneously and uniformly distribute the gel without formation of air bubbles. The auxiliary plate 16 provides support for the top plate 20 when there is only a small overlap between the plates 18 and 20.

FIG. 3 shows a comb-shaped multiple sample-introduction device 52, having teeth 54, the free ends of which are pushed below the leading edge 48 of the first mold plate 20. The teeth extend from a holder 56, which is angled upwardly, as shown in FIG. 1. Portions of the teeth 54 are below the leading edge 58. When combs are removed, the freed teeth spaces ultimately permit the introduction of sample material to the gel layer.

The multiple sample-introduction device 52 can be introduced in the initial position, as shown in FIG. 3, or it can be introduced in the final position of FIG. 2. In the latter case, additional narrow sealing strips can be introduced next to the sealing strips 44 from the outside, and shifted with respect to the existing strips. The thickness of these additional strips is approximately 0.1 mm greater than the desired gel thickness, the thickness of the sealing strips 44. As a result of this slight difference in thickness, introduction of the teeth 54 is facilitated in the final position of the first mold plate 20 (see FIG. 2), since the thickness of the teeth 54 corresponds accurately to the thickness of the sealing strips 44. As soon as the teeth 54 are inserted, the additional narrow sealing strips can be removed.

Using the injection syringe 60 of FIG. 3, liquid layer material 62, such as a gel solution, is injected onto the second mold plate 18 near the leading edge 48 of the upper, first mold plate 20. The amount of the prepared solution corresponds to approximately three times the amount of solution which is theoretically required for filling the intermediate space between the mold plates 18 and 20.

In the initial position of FIG. 3, the intermediate space between the mold plates 18 and 20, which is about 5 mm wide, corresponding to the length a of the overlap, is filled instantaneously with the injected gel solution 62 due to the capillary forces which arise between mold plates 18 and 20, since these plates are at a distance of only about 0.02 to 1.5 mm. Then, the first mold plate 20 is moved slowly in the direction of shift A, either by hand or with the aid of the spindle drive 24 shown in FIGS. 1 and 2.

For shifting with the aid of the spindle drive 24, the bridge 34 is first placed onto the first mold plate 20 and the driver 32 is anchored to the bridge 34. During the shift, if necessary, further amounts of gel solution 62 may be introduced with the aid of syringe 60 onto the second mold plate 18 forwardly of the first mold plate 20. In this way, the opening of the intermediate space between the mold plates 18 and 20 is supplied continuously with fresh gel solution near the leading edge 48 of the upper, first mold plate 20. The capillary forces between the mold plates ensure that the intermediate space is always completely filled with gel solution.

At the opening of the intermediate space near the trailing edge 50 of the lower second mold plate 18, air bubbles may enter the intermediate space if the capillary forces are not sufficient or if the velocity of the movement is too high, since the gel solution is moved along in direction A with the first mold plate 20 due to friction. This is especially true in gels longer than about 300 mm.

In order to prevent the entry of air bubbles near the edge 50, additional gel solution is introduced through the inlet 36. If air bubbles are entrained in spite of this, either in the region of the upper leading edge 48 or of the edge 50, the bubble may be eliminated by moving the first mold plate 20 in the direction opposite that of arrow A. The bubbles can then be removed with the aid of a thin, stainless steel band from the opening, or they may spontaneously disappear into the atmosphere.

Also, a sealing strip may be applied to the second mold surface near and parallel to the trailing edge 50. Such an arrangement is shown in FIG. 5, described below.

In this manner, the first mold plate 20 is shifted continuously through the intermediate position of FIG. 1, to the first position shown in FIG. 2. The preparation of a gel layer having a length of 200 mm takes about 1 minute. Since, as the amount of overlap between the plates 18 and 20 increases, larger forces are required to perform the movement, it is advisable to use the spindle drive 24, especially in the case of gel layers longer than 200 mm. The spindle drive 24 can be controlled so that the threaded spindle 26 moves at a constant angular velocity, even if the load changes.

In order to reduce the frictional resistance, thus to increase the processing rate, and in order to reduce the danger of entrainment of air bubbles, one of the mold surfaces of the plates 18 and 20 may be subjected to a pretreatment which renders these surfaces hydrophobic.

In the final position of the first mold plate 20, as shown in FIG. 3, the mold plates 18 and 20 are attached to each other with the aid of the clasp-like clamping apparatus 64. Since the width of the support 12 is smaller than the width of mold plates 18 and 20 and since the lateral guides 22 are spaced from each other in the longitudinal direction, the clamping apparatus 64 can be conveniently applied to mold plates 18 and 20.

The structural unit formed in this way, consisting of the mold plates 18 and 20 with the gel layer between them, is subjected to a polymerization treatment, during which the plates 18 and 20 remain in a horizontal position. The gel measuring plate is then finished and can be sued in an electrophoresis measuring device. For example, individual samples can be introduced dropwise between teeth 54 with the aid of thin-walled capillaries, such as those used for x-ray analysis (A. Müller, Glass and Vacuum Technology, Berlin).

As noted above, it may be desirable to chemically treat at least one mold surface to enhance the adhesion thereof to the gel layer. The following Example describes a method of treating a mold plate to enhance its adhesion to gel layers.

EXAMPLE

The surface of a glass mold plate is washed with a suitable solvent such as acetone, and then dried. Suitable solvents for washing a polyester plate are ethanol or isopropyl alcohol. When a polyester plate is used, the plate may be immersed in a 20% NaOH solution for ten minutes before washing in order to effect a reduction in protein band widths in the ultimate gel layer.

A first solution comprising 3 ml $H_2O$ and 0.3 ml glacial acetic acid is mixed with a second solution which comprises 100 ml ethanol and 0.3 ml of a silane (silicon hydride) to form a treatment solution. A preferred silane is γ-methacryloxy-propyltrimethoxy silane (Wacker-Chemie, Munich). This silane is relatively innocuous and provides excellent results. Hostaphan BN 100 and BN 180 (Kalle) have also been found useful with polyester films and polyacrylamide gels.

Formation of the first and second solutions, and the resulting treatment solution, should be accomplished within about two minutes, and the treatment solution used immediately, since the silane hydrolyzes rapidly.

The treatment solution is applied to the mold surface by spray, by means of a lint-free paper or cloth, or by immersion, and is allowed to remain on the surface for about 2 minutes. The surface is then dried with a lint-free cloth or paper.

Preferably, the surface is then heated for 15 minutes (100° C. for polyester, 120° C. for glass) to provide a dry, spot-free surface. In some cases, the heating step can be omitted.

The plate can be used immediately, or stored for later use. Before use, the plate should be wiped with a lint-free paper or cloth, which has been immersed into ethanol in order to remove excess silane. As soon as the surface is dry, the plate can be used for preparation of the gel.

Figure 6:
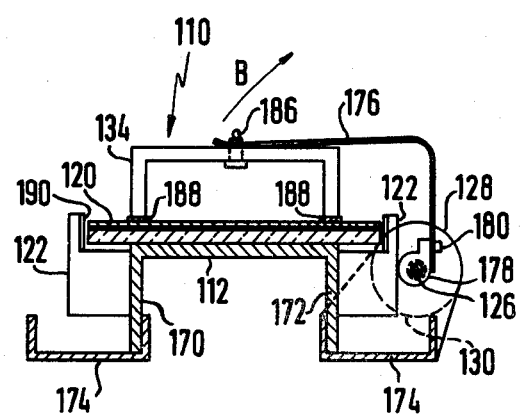
FIG. 6 is a sectional view of the apparatus of FIGS. 4 and 5 along line VI—VI.

A second embodiment of the apparatus for preparing thin layers, designated generally as 110, is shown in detail in FIGS. 4-6. The components of the apparatus 110 whose functions correspond to those of the components of the apparatus 10 in FIGS. 1-3, are designated with the reference numerals of FIGS. 1-3 with 100 added to them.

Referring to FIG. 6, the support 112 is formed by one or more U-tracks which are open toward the bottom. Two collecting tracks 174 are attached to the sides 170 and 172 of the support 112 with screws (not shown). The collecting tracks are U-shaped tracks which are open toward the top, and which protrude transversely from the support 112, as shown in FIG. 6. Therefore, they can catch excess gel solution which drops from the side edges of plates 116, 118 and 120.

The sole plates 128 are attached on both ends of the side 172 of the support 112, on the right in FIG. 6, as well as to the corresponding collecting track 174. The two ends of the threaded spindle 126 are supported on the plates 128. The threaded spindle 126 is driven by electric motor 130, which is secured to the right sole plate 128, as seen in FIGS. 4 and 5.

The connection of the spindle 126 to the first mold plate 120 is provided by bridge 134 and a spring stirrup 176, which is in turn fixed to a spindle nut 178, by means of two screws 180. The bridge 134 is connected to the spring stirrup 176 by means of a removable screw connection 186, which enters a slit 182 punched out at the free end of the spring stirrup 176. Bridge 134 is removably attached to the first mold plate 120 as, for example, with two-sided adhesive tape 188. When the threaded spindle 126 is rotated, the first mold plate 120 is shifted. The connection between the first mold plate 120 and the spindle drive 124 can readily be removed by unscrewing the screw connection 186 and swiveling the spring stirrup 126 in the direction of arrow B in FIG. 6.

FIG. 4 shows the initial position of the first mold plate 120. As described in connection with FIGS. 1-3, the first mold plate 120 is moved from the initial position in the direction of arrow A. L-shaped lateral guide 122 lies against the side edges of the first mold plate 120. In order to facilitate threading, the lateral guides 122 have beveled edges 190.

FIG. 5 shows the first mold plate 120 in its final position. In FIG. 5, the plate 120 is attached to the second mold plate 118 with the aid of clamping devices 164. In order to simplify the illustration, the multiple sample-introduction device which may be disposed near the leading edge 148 of the first mold plate 120 is omitted.

As described above, in the case of relatively long gel layers, there is a danger of the formation of air bubbles in the intermediate space near the trailing edge 150 of the lower, second mold plate 118 (see FIG. 4). In the apparatus 10 of FIGS. 1 and 2, this is prevented by continuously introducing additional gel solution from below near the edge 50. However, this may be relatively expensive. Alternatively, an additional sealing strip 192 (FIG. 5), which extends transversely to the direction of shift A, may be applied to the second mold plate 118, near the trailing edge 150. As a result of this, the intermediate space between the mold plates 118 and 120 is sealed in this region, so that no air bubbles can form. The sealing strip 192 is removed after the preparation of the layer, so that the electrophoresis measurement can be performed.

By simply shifting the first mold plate 120 onto the second mold plate 118 with the continuous introduction of the gel solution near the leading edge 148 of the moving mold plate 120, very thin, bubble-free gel layers can be prepared. The described apparatus has a durable, simple construction which is inexpensive to produce and which can be operated even by inexperienced workers. Several gel layers can be prepared per hour, since only a few minutes are required to prepare a gel layer having a length of 200 mm and a width of 200 mm. Gel layers with a thickness between 0.02 and 1.5 mm can be prepared with lengths that can exceed 200 mm.

The foregoing detailed description is given for clearness of understanding only and no unnecessary limitations should be understood therefrom, as modifications will be obvious to those skilled in the art.

I claim:

1. A method of preparing a thin layer, said method comprising the steps of:
    (a) providing first and second mold elements having first and second mold surfaces, respectively, said first mold element having a straight leading edge;
    (b) disposing said mold elements in a first position wherein said first and second surfaces are parallel and face each other, and are spaced a selected small distance from each other, with said surfaces overlapping each other with said first element's leading edge overlying said second mold surface;
    (c) introducing a liquid layer-forming material to the space defined between said first and second mold surfaces adjacent said leading edge;
    (d) shifting said mold elements relative to each other in a forward direction which is generally perpendicular to the direction of said leading edge from said first position to a second position wherein said mold surfaces are opposed, maintaining said surfaces in parallel relation during the shifting of said element; and
    (e) introducing said liquid to the space defined between said surfaces at a point adjacent said leading edge simultaneously with the shifting of said elements.

2. The method of claim 1 wherein said first element is disposed above said second element with said first surface facing downward, and said liquid material is applied to said surface forwardly of said leading edge.

3. The method of claim 2 wherein said liquid is applied by dropwise addition.

4. The method of claim 1 wherein in the event of formation of a bubble between said surfaces, the direction of shift of said elements is reversed until said bubble is exposed forwardly of said leading edge.

5. The method of claim 1 wherein at least two transversely spaced seals extend between said surfaces in the direction of shift of said elements.

6. The method of claim 5 wherein each said element includes two opposed spaced sides, and each said seal comprises a strip of low friction material having a thickness substantially equal to the spacing between said surfaces and is disposed adjacent opposed sides of said elements.

7. The method of claim 6 wherein said low friction material comprises polytetrafluoroethylene.

8. The method of claim 1 wherein said second mold element includes a trailing edge parallel to the leading edge of said first element, and which underlies said first element when said elements are in the first position, and the space between said surfaces is sealed along said second element trailing edge during the shifting of said elements.

9. The method of claim 8 wherein said seal along said trailing edge comprises a sealing strip applied to said second element along said trailing edge.

10. The method of claim 1 wherein said second element includes a trailing edge underlying said first element when the elements are in their first position and additional liquid material is introduced to the space defined between said surfaces at a point adjacent said trailing edge during the shifting of said elements.

11. The method of claim 1 wherein a third mold element is disposed rearwardly of and adjacent to said second element, said third element having a surface which lies in the plane of said second surface.

12. The method of claim 11 wherein said second and third elements are spaced a short distance from each other.

13. A method of preparing a thin layer, said method comprising the steps of:
(a) providing first and second mold elements having first and second mold surfaces, respectively, said first mold element having a straight leading edge;
(b) pretreating one of said surfaces to render said surface repellant to said liquid material;
(c) disposing said mold elements in a first position wherein said first and second surfaces are parallel and face each other, and are spaced a selected small distance from each other, with said surfaces overlapping each other with said first element's leading edge overlying said second mold surface;
(d) introducing a liquid layer-forming material to the space defined between said first and second mold surfaces adjacent said leading edge;
(e) shifting said mold elements relative to each other in a forward direction which is generally perpendicular to the direction of said leading edge from said first position to a second position wherein said mold surfaces are opposed, maintaining said surfaces in parallel relation during the shifting of said element; and
(f) introducing said liquid to the space defined between said surfaces at a point adjacent said leading edge simultaneously with the shifting of said elements.

14. The method of claim 13 wherein said surface is rendered hydrophobic by said pretreatment.

15. The method of claim 13 wherein said pretreatment step comprises providing said mold surface with a gel-repellent coating.

16. A method of preparing a thin layer, said method comprising the steps of:
(a) providing first and second mold elements having first and second mold surfaces, respectively, said first mold element having a straight leading edge;
(b) pretreating at least one of said surfaces such that the adhesion of said surface to said liquid material is improved;
(c) disposing said mold elements in a first position wherein said first and second surfaces are parallel and face each other, and are spaced a selected small distance from each other, with said surfaces overlapping each other with said first element's leading edge overlying said second mold surface;
(d) introducing a liquid layer-forming material to the space defined between said first and second mold surfaces adjacent said leading edge;
(e) shifting said mold elements relative to each other in a forward direction which is generally perpendicular to the direction of said leading edge from said first position to a second position wherein said mold surfaces are opposed, maintaining said surfaces in parallel relation during the shifting of said element; and
(f) introducing said liquid to the space defined between said surfaces at a point adjacent said leading edge simultaneously with the shifting of said elements.

17. The method of claim 16 wherein said surface is treated with a silane.

18. The method of claim 17 wherein said silane comprises γ-methacryloxy-propyltrimethoxy silane.

19. A method of preparing a thin layer, said method comprising the steps of:
(a) providing first and second mold elements having first and second mold surfaces, respectively, said first mold element having a straight leading edge;
(b) disposing said mold elements in a first position wherein said first and second surfaces are parallel and face each other, and are spaced a selected small distance from each other, with said surfaces overlapping each other with said first element's leading edge overlying said second mold surface;
(c) introducing a liquid layer-forming material to the space defined between said first and second mold surfaces adjacent said leading edge;
(d) introducing a multiple sample introduction device to the space between said surfaces adjacent said first element leading edge, said device comprising a comb-shaped structure having a backbone with a plurality of teeth extending therefrom with spaces between said teeth, said teeth being captured between said elements adjacent said first element leading edge;
(e) shifting said mold elements relative to each other in a forward direction which is generally perpendicular to the direction of said leading edge from said first position to a second position wherein said mold surfaces are opposed, maintaining said surfaces in parallel relation during the shifting of said element; and
(f) introducing said liquid to the space defined between said surfaces at a point adjacent said leading edge simultaneously with the shifting of said elements.

20. The method of claim 19 wherein said multiple sample introduction device is introduced before the shifting of said elements.

21. The method of claim 19 wherein said multiple sample introduction device is introduced after the shifting of said elements.

22. The method of claim 1 wherein said mold elements are pressed together after shifting thereof with a clamping device.

23. The method of claim 1 wherein said liquid is polymerized after shifting of said mold elements.

24. The method of claim 23 wherein said polymerization is carried out with said mold elements disposed vertically or horizontally.

25. A method of preparing a thin layer, said method comprising the steps of:
(a) providing first and second mold elements formed of a material selected from the group consisting of plastic fabrics, cellophane, polystyrene, polyester and glass and having first and second mold surfaces, respectively, said first mold element having a straight leading edge;
(b) disposing said mold elements in a first position wherein said first and second surfaces are parallel and face each other, and are spaced a selected small distance from each other, with said surfaces overlapping each other with said first element's leading edge overlying said second mold surface;
(c) introducing a liquid layer-forming material to the space defined between said first and second mold surfaces adjacent said leading edge;
(d) shifting said mold elements relative to each other in a forward direction which is generally perpendicular to the direction of said leading edge from said first position to a second position wherein said mold surfaces are opposed, maintaining said surfaces in parallel relation during the shifting of said element; and (e) introducing said liquid to the space defined between said surfaces at a point adjacent said leading edge simultaneouly with the shifting of said elements.

26. The method of claim 25 wherein said plastic fabric comprises a polyamide fiber fabric.

27. The method of claim 26 wherein said fabric comprises nylon.

28. The method of claim 25 wherein said material comprises polyester or glass.

29. The method of claim 1 wherein at least one of said mold elements comprises a thermostatically heatable plate.

30. The method of claim 1 wherein at least one of said molded elements comprises a glass plate.

31. The method of claim 29 or 30 wherein the mold surface of said heatable plate or glass plate comprises a polyester film.

* * * * *